United States Patent [19]
Peifer et al.

[11] Patent Number: 6,007,551
[45] Date of Patent: Dec. 28, 1999

[54] ENDOSCOPIC LIGATING APPARATUS

[75] Inventors: Rodney Peifer, Kernersville; Michael K. Simmons, Winston-Salem, both of N.C.; Munir Ahmed, Greenwood, S.C.

[73] Assignee: Wilson-Cook Medical Inc., Winston-Salem, N.C.

[21] Appl. No.: 08/709,423

[22] Filed: Sep. 6, 1996

Related U.S. Application Data

[63] Continuation-in-part of application No. 08/524,069, Sep. 6, 1995, abandoned, and a continuation-in-part of application No. 08/550,531, Oct. 30, 1995, Pat. No. 5,624,453, which is a continuation-in-part of application No. 08/260,380, Jun. 14, 1994, Pat. No. 5,462,559, which is a continuation-in-part of application No. 08/021,036, Feb. 23, 1993, Pat. No. 5,320,630.

[51] Int. Cl.$^6$ .................................................. A61B 17/10
[52] U.S. Cl. ........................... 606/140; 606/141; 606/139
[58] Field of Search ................................... 606/139, 148, 606/140, 141, 135

[56] References Cited

U.S. PATENT DOCUMENTS

| | | |
|---|---|---|
| 3,687,138 | 8/1972 | Jarvik . |
| 3,911,923 | 10/1975 | Yoon . |
| 4,230,116 | 10/1980 | Watson . |
| 4,374,523 | 2/1983 | Yoon . |
| 4,493,319 | 1/1985 | Polk et al. . |
| 4,735,194 | 4/1988 | Stiegmann . |
| 4,744,158 | 5/1988 | Berchem et al. ..................... 37/142 R |
| 4,796,626 | 1/1989 | DeVries .................................. 606/148 |
| 5,100,419 | 3/1992 | Ehlers . |
| 5,207,690 | 5/1993 | Rohrabacher . |
| 5,236,434 | 8/1993 | Callicrate .............................. 606/135 |
| 5,269,789 | 12/1993 | Chin et al. . |
| 5,318,578 | 6/1994 | Hasson ................................... 606/148 |
| 5,356,416 | 10/1994 | Chu et al. ............................... 606/140 |
| 5,398,844 | 3/1995 | Zaslavsky et al. ..................... 606/140 |
| 5,411,508 | 5/1995 | Bessler et al. ......................... 606/153 |
| 5,462,559 | 10/1995 | Ahmed ................................... 606/140 |
| 5,507,797 | 4/1996 | Suzuki et al. . |
| 5,575,801 | 11/1996 | Habermeyer et al. ................. 606/148 |
| 5,664,949 | 9/1997 | LeGuin .................................... 439/22 |

*Primary Examiner*—Michael Buiz
*Assistant Examiner*—Tina T. D. Pham
*Attorney, Agent, or Firm*—Woodard, Emhardt, Naughton, Moriarty & McNett

[57] ABSTRACT

An endoscopic ligating apparatus is provided that can be used percutaneuously to dispense multiple ligating bands or rings about several lesions. In one embodiment, a barrel supporting a plurality of bands stretched around its circumference is removably engaged to the insertion end of an endoscope. A trip wire extends through a working channel of the endoscope and includes a plurality of strands extending from the distal end of the barrel and wrapped around the end of the barrel. The ligating bands are situated over the strands, while the strands are provided with beads disposed adjacent the bands. As tension is applied to the trip wire by way of an activating mechanism, the strands retract within the barrel so that the beads draw the ligating bands successively to the end of the barrel. In one embodiment, the activating mechanism includes a mounting component that stably mounts the mechanism to a variety of endoscopes. The activating mechanism can be manually operated and can include a one-way clutch that can be selectively engaged to restrict the rotation of a spool upon which the trip wire is wound. In another aspect of the invention, an irrigation adapter can be supplied to provide irrigation or aspiration through the activating mechanism and working channel of the endoscope.

12 Claims, 9 Drawing Sheets

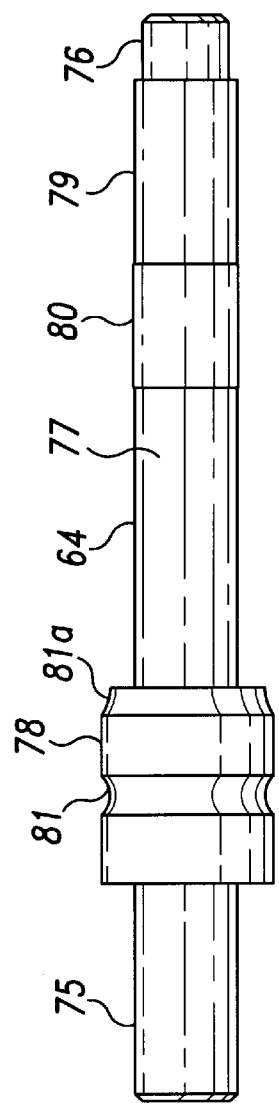
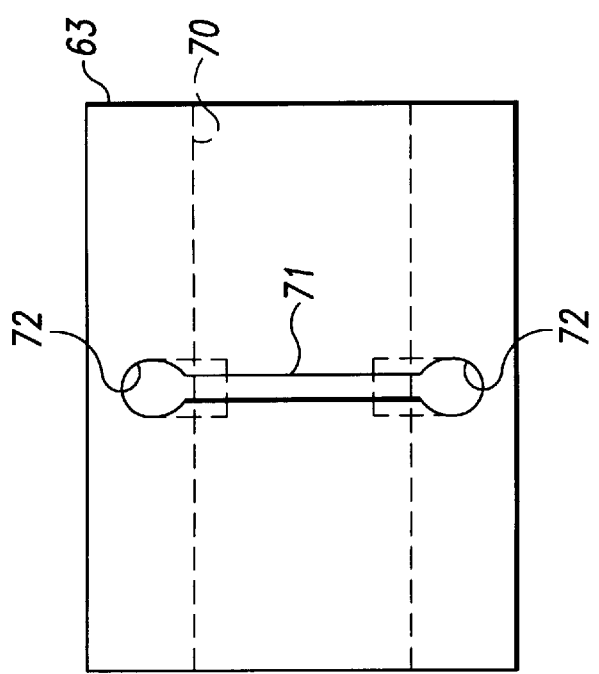

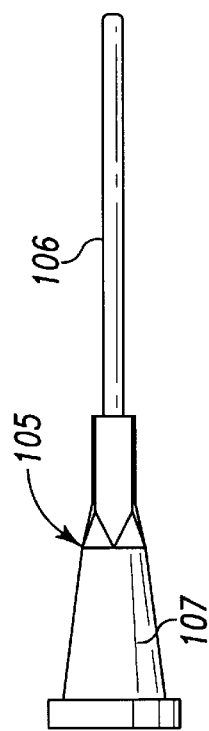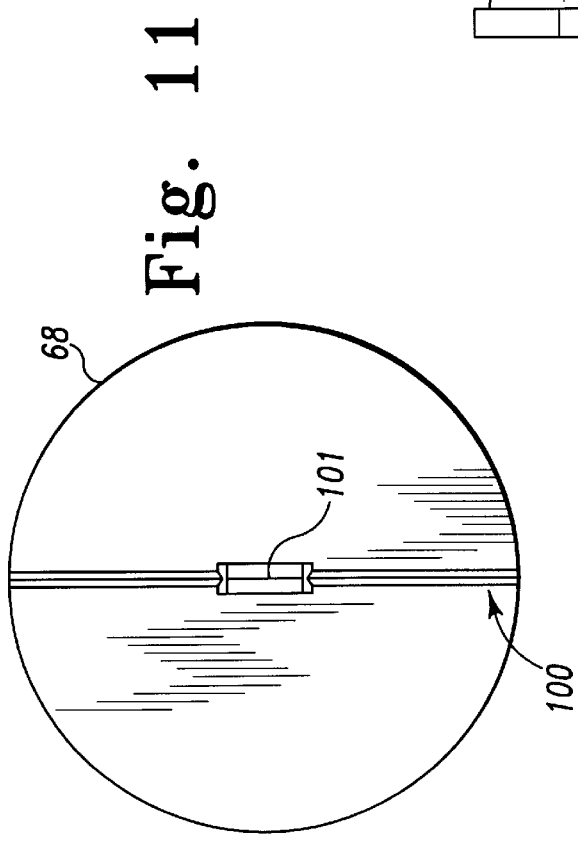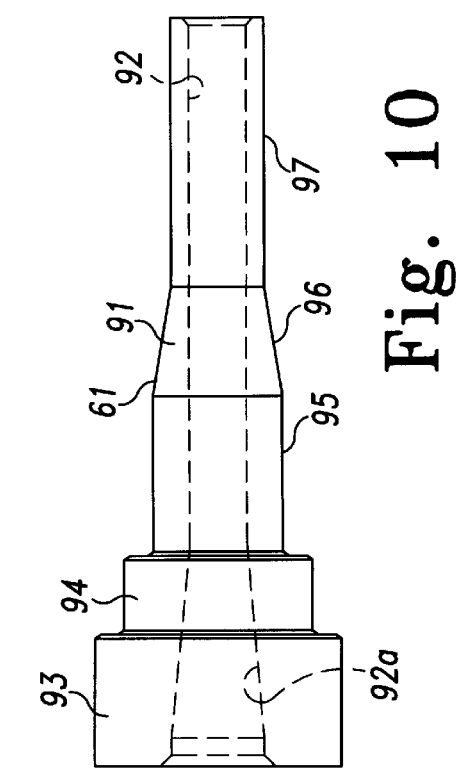

ENDOSCOPIC LIGATING APPARATUS

REFERENCE TO RELATED APPLICATIONS

This application is a continuation-in-part of U.S. patent application Ser. No. 08/524,069, filed on Sep. 6, 1995, now abandoned and is also a continuation-in-part of U.S. patent application Ser. No. 08/550,531, filed on Oct. 30, 1995, now U.S. Pat. No. 5,624,453 which is a continuation-in-part of U.S. patent application Ser. No. 08/260,380, filed on Jun. 14, 1994, now issued as U.S. Pat. No. 5,462,559, which is a continuation-in-part of U.S. Ser. No. 08/021,036, now U.S. Pat. No. 5,320,630, filed on Feb. 23, 1993.

BACKGROUND OF THE INVENTION

The invention relates to an apparatus or instrument for ligating lesions such as for ligating mucosal and submucosal lesions within a hollow organ of the body, such as the alimentary tract. More particularly, the invention relates to an apparatus adapted for use in conjunction with an endoscope.

The endoscopic treatment of lesions presently encompasses a variety of techniques such as electrocauterization, laser photocoagulation, heat therapy by the application of heat probes, and sclerotherapy which involves the injection of medicine into a target varix by a needle passed through the working channel of the endoscope. A further, widely used and increasingly promising technique involves the ligation of lesions, wherein mucosal and submucosal tissue is strangulated by an elastic ligature.

A variety of instruments for effecting the ligation of body tissue by the application of an elastic ring are well known in the prior art. Some of these instruments, because of their rigidity and size, are suited only for treatment of lesions that are in the external regions of the body or in the shallow body cavities. Others are particularly suited for the ligation of tissue in the abdominal cavity, such as for tubal ligation, when the abdominal cavity has been opened surgically.

U.S. Pat. No. 3,760,810 to Van Hoorn discloses an endoscope-equipped instrument comprising a device with two tubes mounted one inside the other, with the inner tube protruding at the front of the outer tube. Means are included to move the outer tube forwardly relative to the inner tube and cause an elastic cord to be dislodged and placed about the tissue to be ligated. In U.S. Pat. No. 4,257,419, there is disclosed an instrument for ligating hemorrhoids, wherein a suction tube fitted inside a proctoscope provides means for sucking the hemorrhoid into a suction cavity where a ligating ring is applied. Both of these instruments are rigid devices suited for treating lesions close to the external regions, and both are equipped with only a single elastic ring for treating a single lesion.

There are also instruments in the prior art which employ laparoscope-assisted means for ring ligation such as shown in U.S. Pat. Nos. 4,257,420 and 4,471,766, wherein the instruments are each equipped with a single elastic band and utilize forceps to position the tissue for ring ligation.

In U.S. Pat. No. 3,870,048, there is disclosed a ring applicator device having forceps slidably mounted in a cylinder for grasping the fallopian tube and including means for displacing an elastic ring to effect a ligation of tissue. While this device can be equipped with a plurality of elastic rings, its rigidity precludes its use with a flexible endoscope for treating the deeper regions of an internal organ, such as the alimentary tract.

A flexible endoscopic instrument used for ligation purposes as disclosed in U.S. Pat. No. 4,735,194, comprises a flexible fiberoptic endoscope to which is secured an outer tube and an inner tube reciprocally movable therein. A trip wire is fastened to the inner tube to provide rearward motion to the inner tube to cause an elastic ring fitted about the inner tube to slide off and effect ligation. While this instrument is suitable for ligating lesions deep within the alimentary tract, it can only be used to treat but one lesion during a single insertion of the instrument.

In many instances, however, there are a number of lesions present in the organ being treated, such as the esophagus, stomach or colon. If an endoscopic instrument equipped with only one elastic ring is used, the treatment of multiple lesions in the same organ requires withdrawal of the endoscope after the placing of each elastic ring about a lesion, reloading the endoscope with a ring, and reinsertion of the endoscope back into the organ to repeat the procedure for placing an elastic ligating ring about each additional lesions. In addition to being time consuming and an associated concern for blood loss when there are bleeding lesions, there are other disadvantages associated with the repetitions of this procedure. The instrument, when withdrawn from the body, is usually covered with blood and mucous. Furthermore, each time the instrument is reinserted into the organ, it becomes necessary to relocate a lesion to be treated and to orient the instrument with respect thereto. In some cases where considerable blood and mucous are present, the relocating of the instrument is a tedious and difficult task.

SUMMARY OF THE INVENTION

A flexible endoscopic instrument is provided with a plurality of elastic ligating bands mounted on a barrel of an endoscopic ligator affixed in coaxial relation to the insertion end of an endoscope. The bands are adapted to be dislodged therefrom in sequence at selectively controlled times for treating multiple lesions during a single insertion of the endoscope into a body organ. In one embodiment, the endoscope is equipped with illumination and viewing means to facilitate orientation of the instrument in the body organ, and longitudinally extending tubular passages comprising channels through which objects may be passed and suction applied for drawing lesion tissue into the tubular end of the endoscope to facilitate ligation of the lesion.

The endoscope also includes a working channel through which a flexible actuating cable or trip wire extends. In one embodiment, the trip wire includes a plurality of cords or strands that are free at the insertion end of the endoscope and braided together to form a single strand at the proximal end of the endoscope. In one embodiment, the plurality of strands are each folded over the distal end of the barrel with their respective free ends extending in the longitudinal direction of the barrel and being angularly spaced relative to one another with respect to the axis of the barrel. A plurality of elastic ligating bands are placed in stretched condition about the outside of the barrel at longitudinally spaced locations thereon and over the strands which lay along the barrel.

In one aspect of the invention, each of the strands is provided with a number of beads at predetermined spaced locations thereon and against each of which an elastic band is placed. The strands can be simultaneously retracted by pulling the single braided strand to pull the rings over the distal end of the barrel in controlled sequence. In another aspect, a slack length is provided in the strands between each pair of adjacent elastic rings. In this manner, a small pulling force is required to dislodge any one of the ligating bands from the tube. Accordingly, each of the elastic bands can be dislodged from the endoscope and placed in ligating relation to a lesion when lesion tissue is drawn into the innermost of the tubular members by a suction force applied through the suction channel and each of the bands can be applied to a single or multiple lesions in the body organ during a single insertion of the endoscope.

In a further aspect of the invention, a loading catheter is provided that is adapted for insertion through the working channel of the endoscope. The loading catheter includes loading hooks mounted at opposite ends of a tubular body. The loading hooks are configured to engage a bead or a knot, affixed at the proximal activation end of the trip wire. A hook of the loading catheter can project from the insertion end of the endoscope and working channel and the locking knot of the trip wire engaged in the hook. The loading catheter is withdrawn through the endoscope to pull the trip wire through to the proximal end.

An activating mechanism is provided in one embodiment of the invention to which the trip wire is engaged. In one embodiment, the activating mechanism includes a spool adapted to receive the trip wire, and particularly the locking bead, to permit winding of the trip wire onto the spool. One feature of the invention contemplates a one-way clutch to restrict rotation of the spool to one direction when the trip wire is being retracted to dispense ligating bands. In one specific embodiment, the spool is mounted on a drive pin that is configured with two portions of different diameter disposed within the one-way clutch. One portion has a diameter sufficiently small to permit freewheel rotation of the spool, that is, rotation in either direction. The second portion has a diameter to engage the clutch to limit rotation of the drive pin and spool to a single direction.

Certain benefits of the present invention are realized by a mounting component that is used to mount the activating mechanism to the endoscope. The mounting component can include a stem that is configured to fit within the working channel of the endoscope. The stem is configured to provide a stable mount for the activating mechanism on the endoscope to facilitate operation of the mechanism to dispense ligating bands. In one feature, the activating mechanism and the mounting component can be configured to receive an irrigation adapter to permit irrigation/aspiration of the working channel even when the trip wire is extending and operable therethrough.

One object of the present invention is to provide an endoscopic ligating apparatus that is capable of dispensing multiple pre-loaded ligating bands. A further object is achieved by features of the trip wire that permits a simple, yet effective, construction.

Certain aspects of the invention allow the ligating apparatus to beneficially provide for simple manual operation to dispense a plurality of ligating bands. A further benefit is contemplated by features of the activating mechanism that allows it to be stably mounted to a wide variety of endoscopes.

Another object of the invention is to provide a simple and efficient device to load the trip wire and endoscopic ligator. Other objects and particular benefits of the present invention can be readily discerned from the following written description and accompanying figures.

BRIEF DESCRIPTION OF THE DRAWINGS

FIG. 8 is a side view of the drive spool 63 of activating mechanism 60 of FIG. 7.

FIG. 9 is a side view of the drive pin 64 of activating mechanism 60 of FIG. 7.

FIG. 10 is a side view of one embodiment of the mounting component 61 of activating mechanism 60 of FIG. 7.

FIG. 11 is a top view of seal 68 of activating mechanism 60 of FIG. 7.

FIG. 13 is a side view of an irrigation adapter 105 for in conjunction with the activating mechanism 60 of FIG. 7 provide irrigation through the working channel.

DESCRIPTION OF THE PREFERRED EMBODIMENTS

Figure 1:
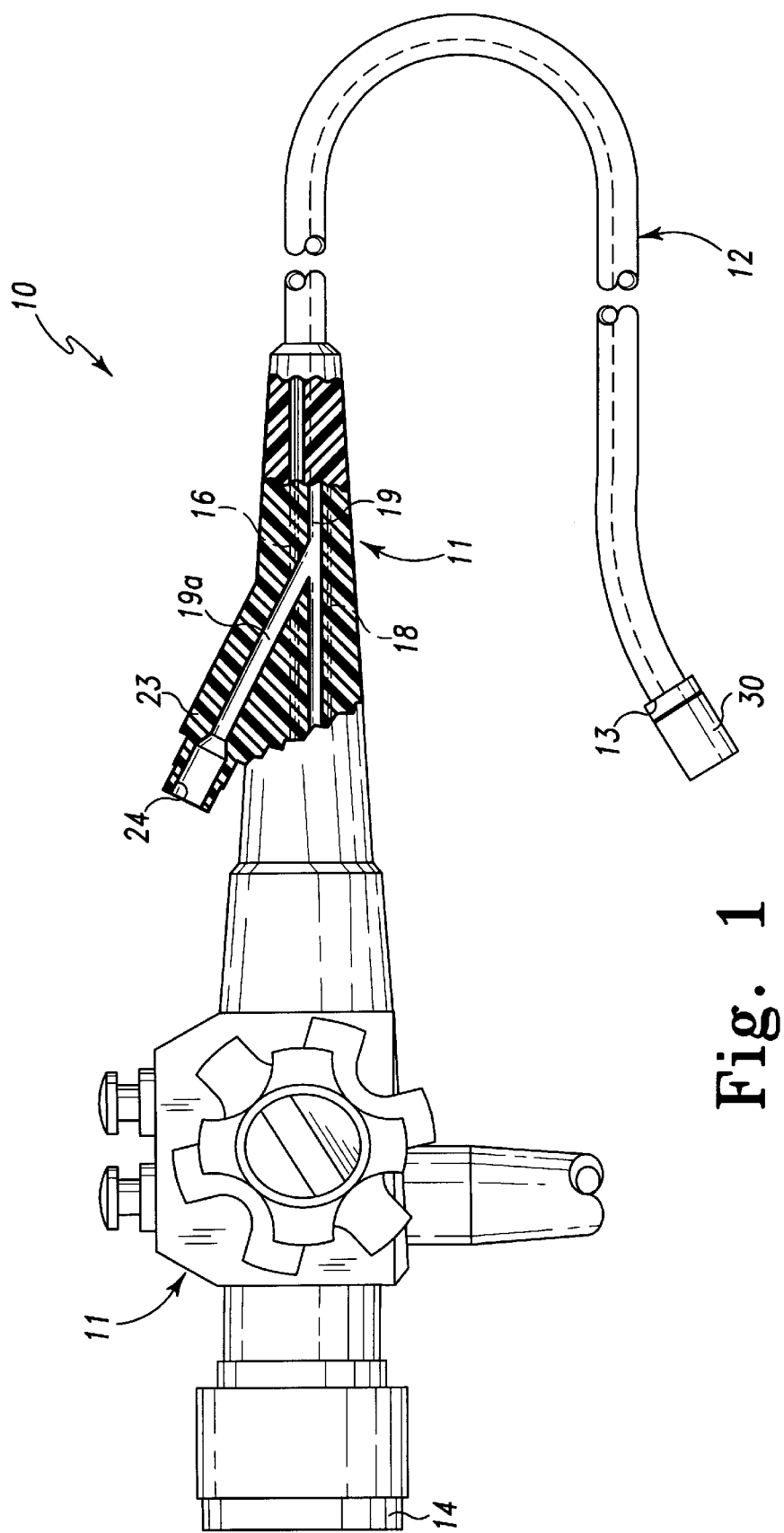
FIG. 1 is a side elevational view, partly in section, of an endoscopic ligating apparatus 10 or instrument according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, and any alterations or modifications in the illustrated device, and any further applications of the principles of the invention as illustrated therein are contemplated as would normally occur to one skilled in the art to which the invention relates.

The present invention contemplates an endoscopic ligating apparatus or instrument that is capable of discharging a plurality of ligating bands onto lesions within the body without having to remove and reinsert the apparatus. In particular, the invention contemplates an apparatus that utilizes a flexible endoscope with an endoscopic ligator disposed at the insertion end of the endoscope. A plurality of bands are disposed about the circumference of the ligator and are dispensed by way of a trip wire structure with a plurality of distally extending strands. The trip wire structure is configured to successively engage each of the ligating bands or rings and apply a motive force to pull the bands off of the tubular body of the ligator.

In one aspect of the invention, a trip wire structure is configured for removing the ligating bands by way of a simple construction. In another aspect, a loading catheter is provided for loading the trip wire through the flexible endoscope. In yet another aspect of the invention, an activating mechanism is provided that allows for manual operation or activation of the trip wires. The activating mechanism can be readily and stably engaged to a variety of flexible endoscopes.

Referring now to FIG. 1, a flexible endoscopic apparatus or instrument 10 is depicted which has a length that permits access to the deeper regions of a hollow body organ. In certain embodiments, the flexible endoscope can be sized for insertion into the alimentary tract. In accordance with one embodiment, the apparatus 10 includes a conventional endoscope with an operating control section 11 and a flexible section 12, terminating at a distal insertion end 13. The operating control section 11 includes a viewing end 14 remote from the insertion end 13, through which the ligating procedure can be directly observed.

Figure 3:
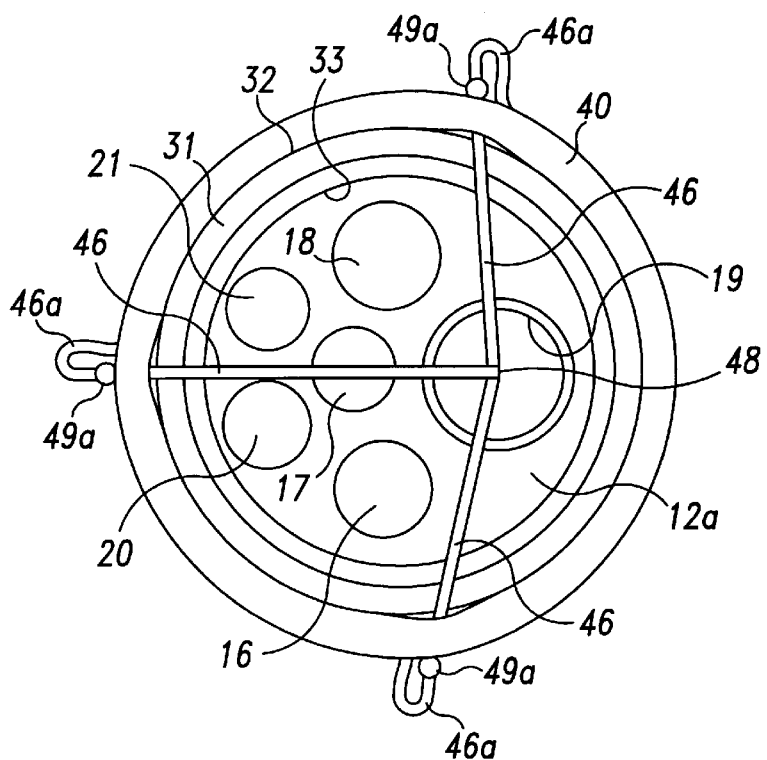
FIG. 3 is an end view of the endoscopic ligator 30 of FIGS. 1 and 2.

Referring to FIGS. 1 and 3, the endoscopic instrument 10 can include a plurality of channels extending from the operating control section 11 and through the flexible section 12 to the insertion end 13. For example, the instrument 10 can include an illumination channel 16 through which is inserted a fiberoptic cable for the transmission of light from a light source. A viewing channel 17 can also be provided with a fiberoptic cable for viewing purposes, while a third channel 18 can be provided for application of suction at the surgical site. The endoscopic instrument 10 can also include a working channel 19 through which a plurality of tools and instruments can be extended, an irrigation channel 20 to allow delivery of fluid to the ligation site, and an air channel 21 that can be used to deliver pressurized air, such as for cleaning the lens at the insertion end of the viewing channel 17.

In one embodiment, the endoscopic instrument 10 also includes an auxiliary port portion 23 having a proximal opening 24. The working channel 19 extends into the auxiliary port 23 by way of a working channel extension 19a. Each of the channels preferably opens at the distal or insertion end 12a of the flexible section 12 of the endoscopic instrument 10.

The endoscope forming part of the instrument 10 of FIG. 1 can be of many different types. For example, the endoscope can be of the type commercially provided by Olympus, Pentax, or Fujinon. While most of the working components of these endoscopes are similar, each may have a different configuration for the proximal opening 24 and the auxiliary port 23. Each of these specifically identified endoscopes, and other commercially available endoscopes, utilize different sealing members (not shown) at the proximal opening 24 of the auxiliary port 23. It is understood that the various aspects of the present invention accommodate the secure attachment to various configurations and dimensions of a variety of endoscopes.

Figure 2:
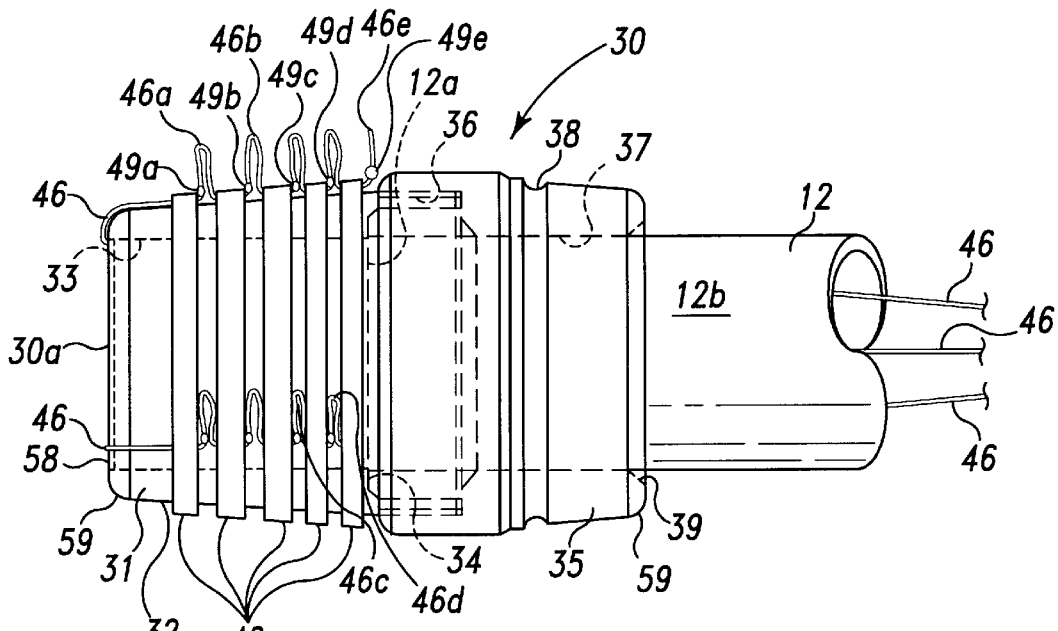
FIG. 2 is a side elevational view showing an endoscopic ligator 30 according to one embodiment of the invention, disposed at the end of an endoscope, such as the endoscope depicted in FIG. 1.

Referring now to FIG. 2, details of the endoscopic ligator 30 can be discerned. In this embodiment, ligator 30 is disposed at the insertion end 12a of the flexible section 12 of the endoscope. In one specific embodiment, the ligator 30 includes a barrel 31, which can be formed of a transparent plastic material for enhancing the illumination and field of vision from the insertion end of the endoscope. Alternatively, other materials suitable for insertion into the human body can be contemplated, including stainless steel. The material of the barrel 31 should be sufficiently strong or rigid to support a plurality of ligating bands or rings 40 stretched onto the outer surface 32 of the barrel. The ligating bands are typically formed of an elastic material, preferably a rubber material, or an inert non-toxic plastic composition.

The barrel 31 of the ligator 30 includes a bore 33 defined therethrough. The bore 33 further forms an internal annular flange 34 that is sized to abut the insertion end 12a of the flexible section 12 when the ligator 30 is mounted thereto.

The barrel 31 is preferably removably mountable to the insertion end 12a of the flexible endoscope section 12. In this manner, barrels pre-loaded with ligating bands or rings can be made available for mounting on the endoscope. In one particular aspect of the invention, the ligator 30 also includes a friction adapter 35 which is configured to securely connect the barrel 31 to insertion end 12a. The friction adapter 35 includes first mating bore 36 that is sized to provide a friction fit around the outer surface 32 and at the proximal end of the barrel 31. The adapter 35 also includes a second mating bore 37 having a diameter suitable to provide a friction fit about the cylindrical surface 12b of the flexible endoscope section 12.

In use, the endoscopic ligator 30 is preferably provided separately from the endoscopic instrument 10 with the friction adapter 35 already mounted about the outer surface 32 of the barrel 31. At an appropriate time in the use of the flexible endoscopic ligation instrument 10, the ligator 30 can be mounted about the cylindrical surface 12b of the flexible endoscope section 12 by pressing the friction adapter 35 onto the surface 12b. A gripping groove 38 can be provided in the outer surface of the friction adapter 35 to offer a gripping surface to facilitate telescopically pushing the friction adapter 35 onto the cylindrical surface 12b of the flexible endoscope section 12. The second mating bore 37 can also be provided with a flared region 39 to facilitate insertion of the insertion end 12a of the endoscope into bore 37.

In this preferred embodiment, the endoscopic ligator 30 has an adapter 35 that mounts the barrel 31 supporting the ligating bands 40 onto the flexible endoscope section 12. In one specific embodiment, the adapter engages the barrel to the endoscope by way of friction. While the barrel 31 is preferably formed of a hard plastic clear polycarbonate such as CALIBRE® from Dow Chemical Co., the friction adapter 35 is preferably formed of a resilient material, such as a plastic or a polyurethane having a shore hardness of approximately 80A to enable it to be affixed firmly with a secure friction fit over slightly varying ranges of outer diameters of various standard flexible endoscopes. One material suitable for the friction adaptor is Tecoflex® by Thermetics. Other materials or configurations of the adapter 35 can be contemplated, with the understanding that the adapter must provide a firm engagement between the barrel 31 of the ligator 30 and the insertion end of the flexible endoscope section 12. For example, it may be contemplated that a separate elastic band can be engaged within the gripping groove 38 of the friction adapter 35 to clamp the adapter to the flexible endoscope section 12.

Figure 4:
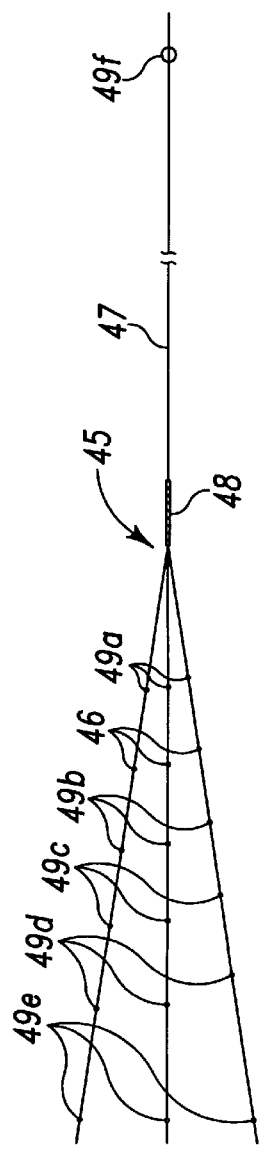
FIG. 4 is a side view of a trip wire 45 used with the endoscopic ligating apparatus 10 of FIG. 1.

In a further aspect of the invention, the apparatus 10 is provided with a trip wire 45, which is shown in detail in FIG. 4 and depicted in use in FIGS. 2 and 3. In one embodiment, the trip wire 45 includes a plurality of strands 46 that can be distributed around the outer surface 32 of the barrel 31. In one specific embodiment, three such strands are provided that are oriented equidistant around the circumference of the outer surface 32. As shown most clearly in FIG. 2, each of the strands passes underneath each of the plurality of ligating bands 40. In one embodiment, the strands are disposed about the outside of barrel 31 to form loops 46a between adjacent ligating bands as shown in FIG. 2. It is preferred, however, that after placement of the most proximal band 46d, the barrel 31 is rotated in one direction (e.g., clockwise) approximately 60° so that the strands 46 wrap around the outside of barrel 31. The next ligating band is then affixed over barrel 31 and over the strands and against the next set of beads 49d so that the next ligating band 40 rests up against the next set of beads 49d. Barrel 31 is then rotated approximately 60° in the opposite direction (e.g., counter-clockwise), and so on. In this manner, the strands 46 are caused to lay flat around the periphery of barrel 31 in between each successive band 40 so they do not extend outwardly from ligator 30. For a description of the remainder of this invention, reference will be made to a configuration with the loops 46a through 46d, it being understood that the preferred embodiment contemplates loading the bands 40 and strands 46 so that the strands 46 between adjacent bands lies flat along the outside of barrel 31.

Also, the present embodiment is shown configured for five ligating bands 40. In the preferred embodiment, ligator 30 is preloaded with six ligating bands 40. It is to be understood, however, that the ligator 30 of the present invention may be configured to deliver even more than six bands depending on the size of the bands, barrel 31, the endoscope, or any other limiting component. Preferably, the strands are formed into loops 46a between adjacent ligating bands. While the bands 40 are depicted in FIG. 2 as being separated by a uniform distance, the bands can be pressed immediately adjacent each other in side-by-side relation with the strand loops 46a projecting therebetween, or the bands can be non-uniformly separated along the length of the barrel 31. It is understood that the arrangement of the bands 40 on the barrel 31, as well as the form and length of the loops 46a–46d between each of the bands, will affect the manner and timing in which the ligating bands 40 are dispensed from the ligator 30.

Returning to FIG. 4, the trip wire 45 includes a braided section 47 in which each of the plurality of strands 46 is braided to essentially form a single strand. In one specific embodiment, the braided section 47 includes an additional strand that does not extend all the way to the ligator 30. This additional strand can be used to provide a wrapped section 48 between the separate strands 46 and the braided strands 47. This wrapped section 48 will then prevent unravelling of each of the separate strands 46 from the braided section 47.

In a further aspect of the present invention, a plurality of beads 49a–e are affixed at predetermined distances along each of the trip strands 46, as shown most clearly in FIG. 4. As shown in FIG. 2, the beads 49a–d are situated to define the front of each of the loops 46a–d, and thus to separate the plurality of ligating bands 40. A final bead 49e is affixed at the end 46e of each trip strand 46. Each of the beads 49a–e thus facilitates ejection of a corresponding ligating band 40 from the barrel 31. In one aspect, the beads 49a–e replace the knots formed in the trip wire strands as disclosed in U.S. application Ser. No. 08/260,380, discussed above and can operate in a similar manner. In the preferred embodiment, each of beads 49a–49e are affixed to strands 46 by injection molding. In one embodiment, the strands 46 are secured within two mold halves (not shown) that are clamped together and the plastic material is injection molded into the molds to form each individual bead 49a–49e.

The dispensing of each of the ligating bands 40 can be effected by pulling the trip wire 45 through endoscopic instrument 10. As the trip wire 45 is pulled, each of the trip strands 46 are also pulled into the endoscope so that all of the beads 49a adjacent the first one of the ligating bands 40 are pulled until the loops 46a are straightened. The length of the loops 46a in each of the plurality of strands 46 can be calibrated so that each of the strands is fully straightened once the ligating band 40 is dispensed over the end of the barrel 31. Each of the successive loops 46b–46d can also be appropriately sized so that the same phenomenon occurs for dispensing of each successive ligating band. In other words, in one specific embodiment, the loops 46a–46d become successively larger since the associated locking bead 49a–e and corresponding ligating band 40 must travel farther along the outer surface 32 of the barrel 31 to dispense the ligating band. Alternatively, the loops 46a–d can have uniform lengths so that the successive ligating bands 40 will be drawn closer toward the end of the barrel as the immediately prior ligating band is dispensed from the ligator 30.

In one specific aspect of the invention, the outer surface 32 of the barrel 31 is tapered approximately 3° toward the dispensing end 30a of the ligator 30. It has been found that a sloped surface enhances the ability of the beads 49a–e to pull the bands off of the barrel 31 when the ligating bands, such as the bands 40, have a relatively flat surface in engagement with the outer surface 32 of the barrel 31. Alternatively, the barrel 31 can have a uniform outer diameter, with the understanding that greater pulling force may be required to release the bands 40. As a further alternative, the ligating bands may have a circular cross-section wherein they may more readily slide or roll off the barrel 31. It should also be noted that the leading inner and outer circumferential edges of the distal end of barrel 31 are rounded off at 57 at 58, respectively, as is the proximal circumferential edge 59 of adapter 35. This rounding off helps prevent possible erosion of the vessel wall that is being treated by the ligating instrument 10 of the present invention.

In a preferred embodiment, the trip wire 45 extends through the entire length of the flexible section 12 of the endoscopic apparatus 10 and exits through the opening 24 of the auxiliary port 23. The trip wire 45 may include a knot or locking bead at 49f adjacent the proximal end of the braided strand 47. Since the separate trip strands 46 extend around the dispensing end 31a of the barrel and into the bore 33, some care is preferably taken in the positioning of the strands. Each of the strands extend through the working channel 18 through which the entire trip wire 45 extends. In this instance, as seen most clearly in FIG. 3, the positioning of the strands 46 can affect which of the channels 16–21 is partially obstructed. For example, in the configuration shown in FIG. 3, the viewing channel 17 is partially obstructed by the presence of a trip strand 46. In some instances, this positioning of the strand may be undesirable since it may interfere with a complete view of the working area through the viewing channel 17. While the strands may be repositioned to avoid overlapping critical channels, care should be taken to position the strands uniformly around the circumference of the barrel to provide an even peripheral pulling force to each ligating band 40. It is further understood that additional strands may be provided as desired for a more uniform dispensing action.

Figure 5:
FIG. 5 is a side view of a loading catheter 50 for use in loading the trip wire 45 of FIG. 4 into the endoscopic ligating apparatus 10 of FIG. 1.
Figure 6:
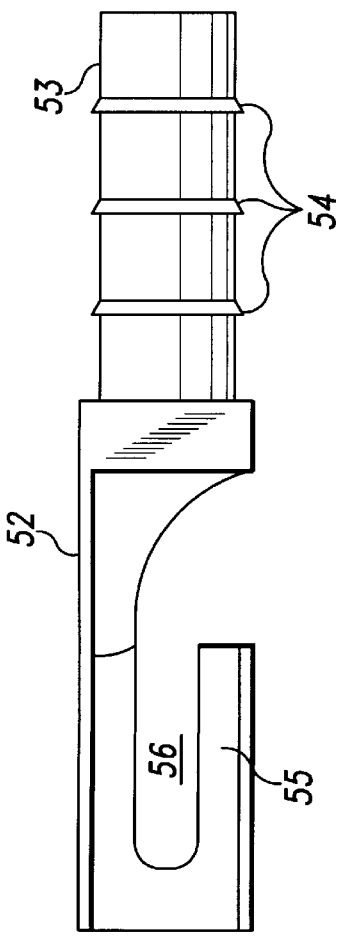
FIG. 6 is an enlarged side view of the loading hook 52 forming part of the loading catheter 50 of FIG. 5.

In a further aspect of the invention, a loading catheter 50 is provided for loading the trip wire 45 through the flexible endoscope section 12. In one preferred embodiment, the loading catheter 50 includes a tubular body 51, as shown in FIG. 5. A loading hook 52 is disposed at the opposite ends of the tubular body 51. The details of the loading hooks 52 are shown in FIG. 6. In one specific embodiment, the loading hooks 52 include a mounting shank 53 having a plurality of annular barbs 54. The mounting shank 53 is adapted to be pressed into the hollow interior of the tubular body 51. The barbs 54 prevent dislodgement or removal of the loading hooks from the body 51. Loading hooks are preferably provided at each end of the loading catheter so that either end of the catheter 50 can be utilized.

Each of the loading hooks 52 includes an arm 55 which curves around to define a slot 56. The slot preferably has a width that is slightly smaller than the outer dimension of locking knot 49f. In one specific embodiment, each of the beads is circular with a diameter of 0.041 inches, while the slot 56 in the loading catheter 50 has a width of 0.025 inches. Also preferably, the loading catheter 50 has an outer diameter that is sized to be received within the working channel 19 of the endoscopic instrument 10. Moreover, the loading catheter 50 has a length that allows one of the catheter hooks to extend beyond the insertion end 12a of the flexible section 12 while its opposite end extends out of the opening 24 of the auxiliary port 23 to be grasped by the operator.

In accordance with one aspect of the present invention, the endoscopic ligation apparatus 10 is used to dispense ligating bands 40 from the ligator 30 about a lesion. In one embodiment, the trip wire 45 can be disposed through the endoscope with its proximal free end and locking knot 49f extending outside the auxiliary port 23. Certainly, the ligating bands 40 can be dispensed by manually pulling the trip wire 45, such as by grasping the locking knot 49f. However, it is more preferable to provide an activating mechanism for applying tension to retract the trip wire 45. The activating mechanism can be used to engage the proximal end of the trip wire 45 at the locking knot 49f and retract or reel in the trip wire 45 to successively dispense ligating bands 40.

Figure 7:
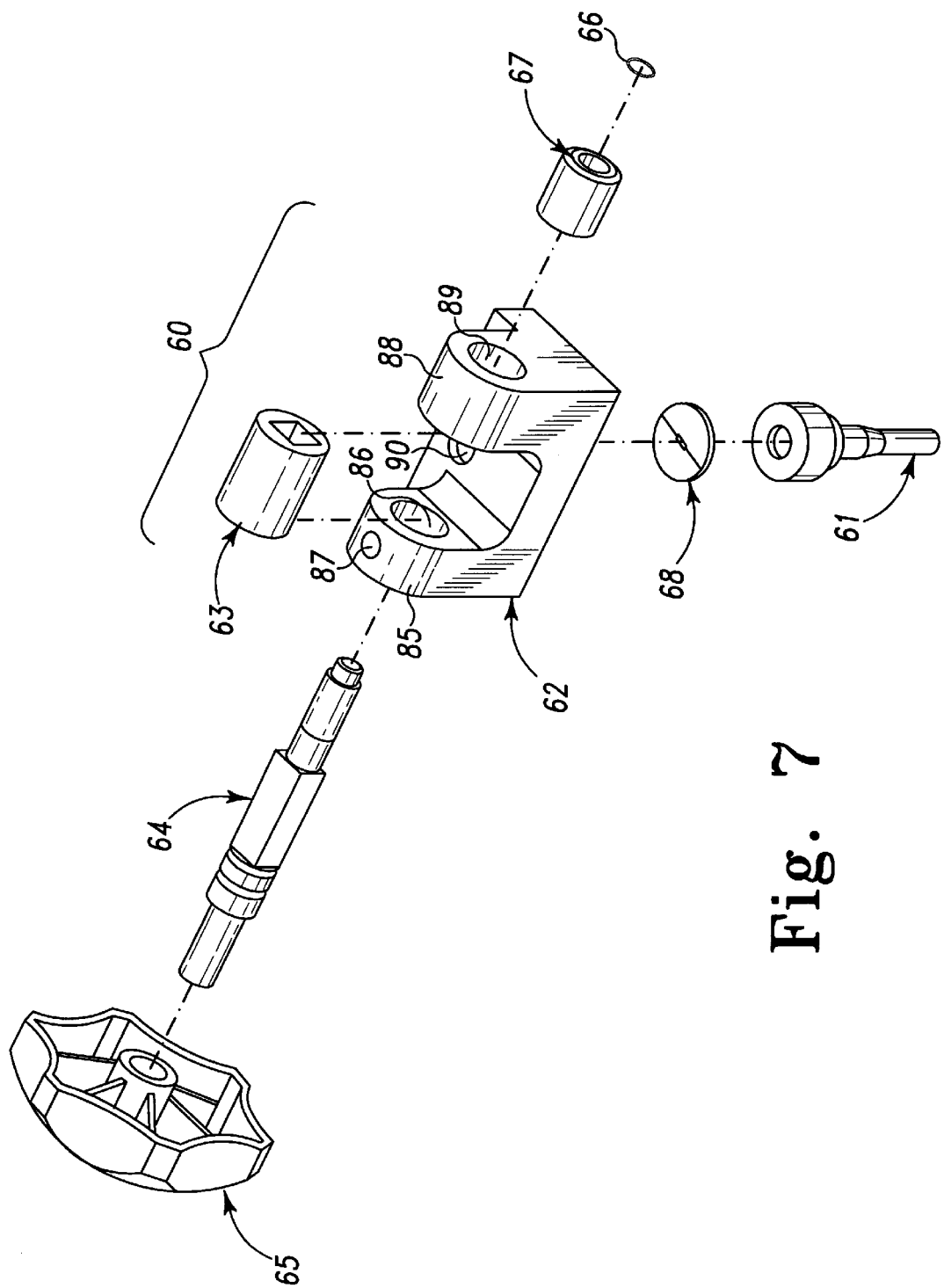
FIG. 7 is an exploded perspective view of an activating mechanism 60 for use in one embodiment with the endoscopic ligating apparatus 10 of FIG. 1 to activate the trip wire 45.

By way of example, an activating mechanism 60, such as that shown in FIG. 7, can include a mounting component 61 and a base portion 62. The mounting component 61 is sized and configured to extend within opening 24 to engage and support the activating mechanism 60 with auxiliary port 23. The mounting component 61 is also connected to the base portion 62. The base portion 62 supports a spool 63 about which the trip wire 45 can be wound to retract the trip wire and dispense the ligating bands 40. The spool 63 is supported for rotation by the base portion 62 by way of a drive pin 64. A knob 65 is engaged to the drive pin 64 at one end to permit manual rotation of the drive pin, while a retainer 66 is affixed to the opposite end of the drive pin 64 to fix the pin within the base portion 62. In one specific embodiment, a one-way clutch 67 is provided through which the drive pin 64 is disposed. The one-way clutch 67 is operable to selectively permit rotation of the drive pin 64, and thereby the spool 63, in a single direction. As further shown in FIG. 7, a seal 68 can be provided between the mounting component 61 and the base portion 62.

Details of one embodiment of the activating mechanism can be seen in FIGS. 8–11. In particular, the spool 63 is shown in FIG. 8. The spool includes a passageway 70 extending through the length of the spool. Preferably, the passageway is non-circular, and in one specific embodiment has a square cross-section. A slot 71 is formed in the outer circumference of the spool 63. The slot 71 terminates at its ends in enlarged recesses 72. The slot 71 is sized and configured to receive the braided strand 47 of the trip wire 45 therein but is too small to permit the knot 49f to pass therethrough. The enlarged recesses 72 are sized and configured to receive the locking knot 49f therein so that the end of the trip wire 45 can be temporarily but securely connected with spool 63. It is of course understood that rotation of the spool 63 allows the trip wire 45 to be wound around the outside of the spool as the wire is drawn through endoscope section 12.

The spool 63 is engaged to the base portion 62 by way of the drive pin 64. In one specific embodiment depicted in FIG. 9, the drive pin includes a mounting end 75 that is adapted to securely receive knob 65. In the preferred embodiment, the mounting end 75 has a surface pattern, such as knurling, to provide firm engagement with the knob 65, and the knob 65 is insert molded right onto the end 75 of drive pin 64. The opposite end of drive pin 64 defines a retainer mounting end 76 that is configured to securely receive retainer 66. In one specific embodiment, the retainer 66 is a flexible cap that is pressed onto the mounting end 76. Alternatively, the retainer 66 can be a snap ring with the mounting end 76 being appropriately configured. At any rate, the drive pin 64 is securely held by the base portion 62 between the knob 65 and the retainer 66.

The drive pin 64 also includes a spool mounting section 77 about which the spool 63 is disposed. Preferably, the spool mounting section 77 has a configuration similar to the configuration of the bore 70 in spool 63. In the specific embodiment, the spool mounting section 77 has a square cross-section to match the square cross-section passageway 70 of the spool 63. It is of course understood that other configurations of the passageway 70 and spool mounting section 77 are contemplated. Most preferably, the passageway and mounting section have mating non-circular cross-sections; however, a press-fit cylindrical mating engagement may also suffice to achieve the objects of the present invention.

The drive pin 64 also includes a bearing portion 78 which defines a detent groove 81 and a detent ridge 81a. At the opposite end of the drive pin 64, a free wheel portion 79 and a one-way drive portion 80 is defined. In the specific embodiment, the drive portion 80 has a diameter that is larger than the diameter of the free wheel portion 79. The one-way drive portion 80 is configured to engage the one-way clutch 67 supported by the base portion 62. The free wheel portion 79 has a diameter that is slightly smaller so that it does not engage the one-way clutch, but simply rotates within the clutch so that the clutch operates as a bearing for the rotation of the drive pin 64.

Figure 12B:
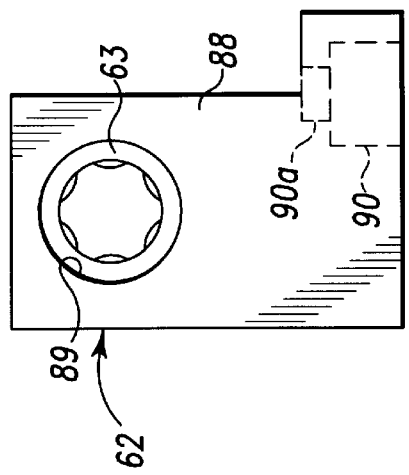
FIG. 12B is an end view of the base portion 62 of FIG. 12A showing the one-way clutch according to one specific embodiment of the present invention.
Figure 12C:
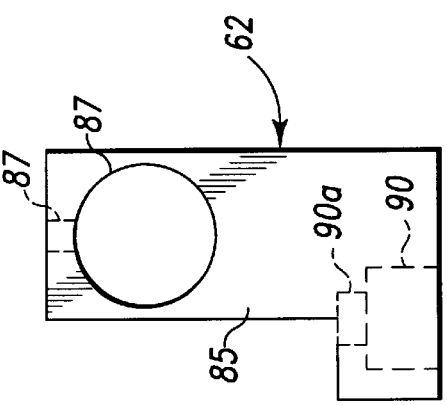
FIG. 12C is an end view of the opposite end of the base portion 62 of FIG. 12B.
Figure 12A:
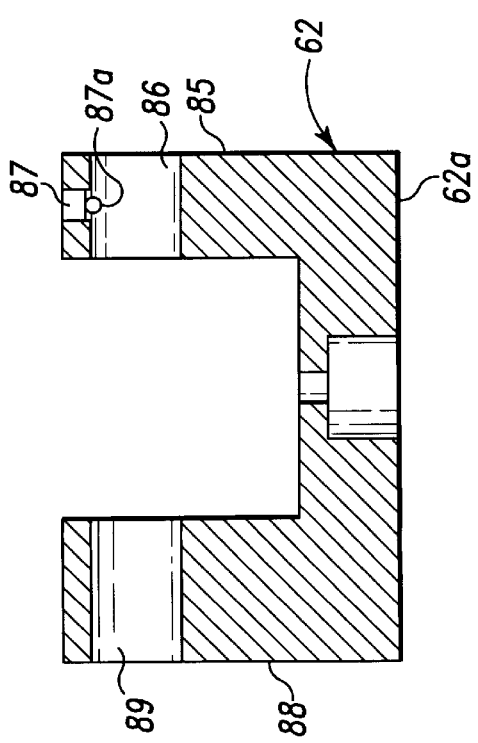
FIG. 12A is a side view of the base portion 62 of activating mechanism 60 of FIG. 7.

Referring back to FIG. 7 and to FIGS. 12A–C, details of the construction of the base portion 62 can be seen. The base portion includes a first arm 85 defining a bearing bore 86 through which the drive pin 64 extends. Specifically, the bearing portion 78 of the drive pin is disposed within the bearing bore 86. The first arm 85 also defines a detent bore 87 that is perpendicular to the bearing bore 86. The detent bore 87 is situated to be juxtaposed over either the detent groove 81 or the detent ridge 81a of the drive pin 64. The detent bore 87 can include a pin or tab 87a or other feature that resiliently engages the detent groove 81 or detent ridge 81a. This detent engagement allows the drive pin 64 to be reciprocated within the base portion 62, and specifically within the clutch 67 so that the free wheel portion 79 or the one-way drive portion 80 can be alternately disposed within the clutch.

The base portion 62 further includes a second arm 88 that defines a clutch bore 89 within which the clutch 67 can be disposed. The mounting component 61 is disposed within a stem bore 90 of the base portion 62. The stem bore 90 can include a reduced diameter portion 90a against which the mounting component 61 and/or seal 68 can bear. Preferably, the seal is compressed between the reduced diameter portion 90a and the mounting component 61 to hold the seal in place.

In one aspect of the invention, the mounting component 61 includes a stem 91 defining a threading bore 92 therethrough, as shown in FIG. 10. The mounting component 61 also includes a coupling portion 93 that is configured to be disposed within the stem bore 90 from the underside 62a (FIG. 12A) of the base portion 62. In the preferred embodiment, the seal 68 is situated on top of the mounting portion 93 as the mounting component 61 is pushed into the bore.

The stem 91 of the mounting component 61 includes an outer sealing portion 94 and a number of auxiliary port mating portions 95–97, each having different diameters and configurations. In one specific embodiment, the outer sealing portion 94 can seat within a sealing member (not shown) that is disposed over the opening 24 of the auxiliary port 23. In one aspect, the outer sealing portion 94 can be configured to create a form fit, or a friction fit, with the sealing member. Alternatively, depending upon the design of the endoscope, the outer sealing portion 94 can engage the outer surface of the auxiliary port of a sealing member.

The first, second and third mating portions 95–97, respectively, can be configured to correspond to the working channel extension 19a at the proximal opening 24. The configuration of the mating portions 95–97 can be varied depending upon the configuration of the auxiliary port 23 and working channel extension 19a of the specific endoscope. The mounting component 61, and particularly the stem 91, is configured to provide a solid and stable mount for the activating mechanism 60. In the specific illustrated embodiment, the mating portions 95–97 are configured with a first diameter portion 95, and tapering diameter portion 96 and a reduced diameter portion 97 to create a press-fit or a friction-fit engagement with the substantially constant diameter working channel extension 19a at the proximal opening 24 of the auxiliary port 23. The coupling portion 93 is also preferably press-fit into the stem bore 90 of the base portion 62 so that, when assembled, the activating mechanism 60 is firmly supported on the endoscopic ligation apparatus 10.

Alternatively, the stem 91 can have other configurations that provide a stable base, although not necessarily a press-fit or friction-fit with the auxiliary port 23. It is further contemplated that some separate device or mechanism can be used to secure the activating mechanism 60 to the endoscope instrument 10. It is important, however, that the activating mechanism 60 be stably mounted on the auxiliary port 23 so that the function and operation of the mechanism and the trip wire 45 is not compromised.

Seal 68 is disposed at the top of the mounting component 61 within the stem bore 90 of the base portion 62. As shown in FIG. 11, seal 68 is configured to maintain a sealed environment within the working channel 19. In one specific embodiment, the seal 68 includes a groove 100 spanning across the diameter of the seal. A slit 101, that permits the exit of trip wire 45 therethrough, is centrally located in the seal 68 along the line of the groove 100. In one specific embodiment, the slit has a width of 0.08 inches so that it provides a close fit around the trip wire 45. The seal is preferably composed of a resilient and flexible material so that the slit 101 can be easily expanded to accept other tools or instruments. In one specific embodiment, the seal 68 is formed of 50–60 durometer silicone.

In a further aspect of the invention, the slit 101 and the seal 68 can be preferably configured to receive an irrigation adapter 105 therethrough. In certain circumstances, it is contemplated that irrigation of the working channel 19 may be necessary even as the activating mechanisms 60 and trip wire 45 are being manipulated. In one embodiment shown in FIG. 13, the irrigation adapter 105 includes a hollow tip 106 integral with a hollow Luer® hub 107. The Luer® hub 107 is configured to mate with a Luer® fitting on an irrigation device of known design. In one specific embodiment, the hollow tip 106 has a length of 1.5 inches so that it extends adequately through the stem bore 90 of the base portion 62, the slit 101 in the seal 68, and into the threading bore 92 of the mounting component 61. The threading bore 92 can include a tapered portion 92a (FIG. 10) to readily accept the irrigation adapter 105. The diameter of the hollow tip 106 is sufficiently small so as not to interfere with the trip wire 45 disposed therein. On the other hand, the interface between the tip 106 and the hub 107 is configured to sealingly engage within the slit 101 of the seal 68.

Figure 14:
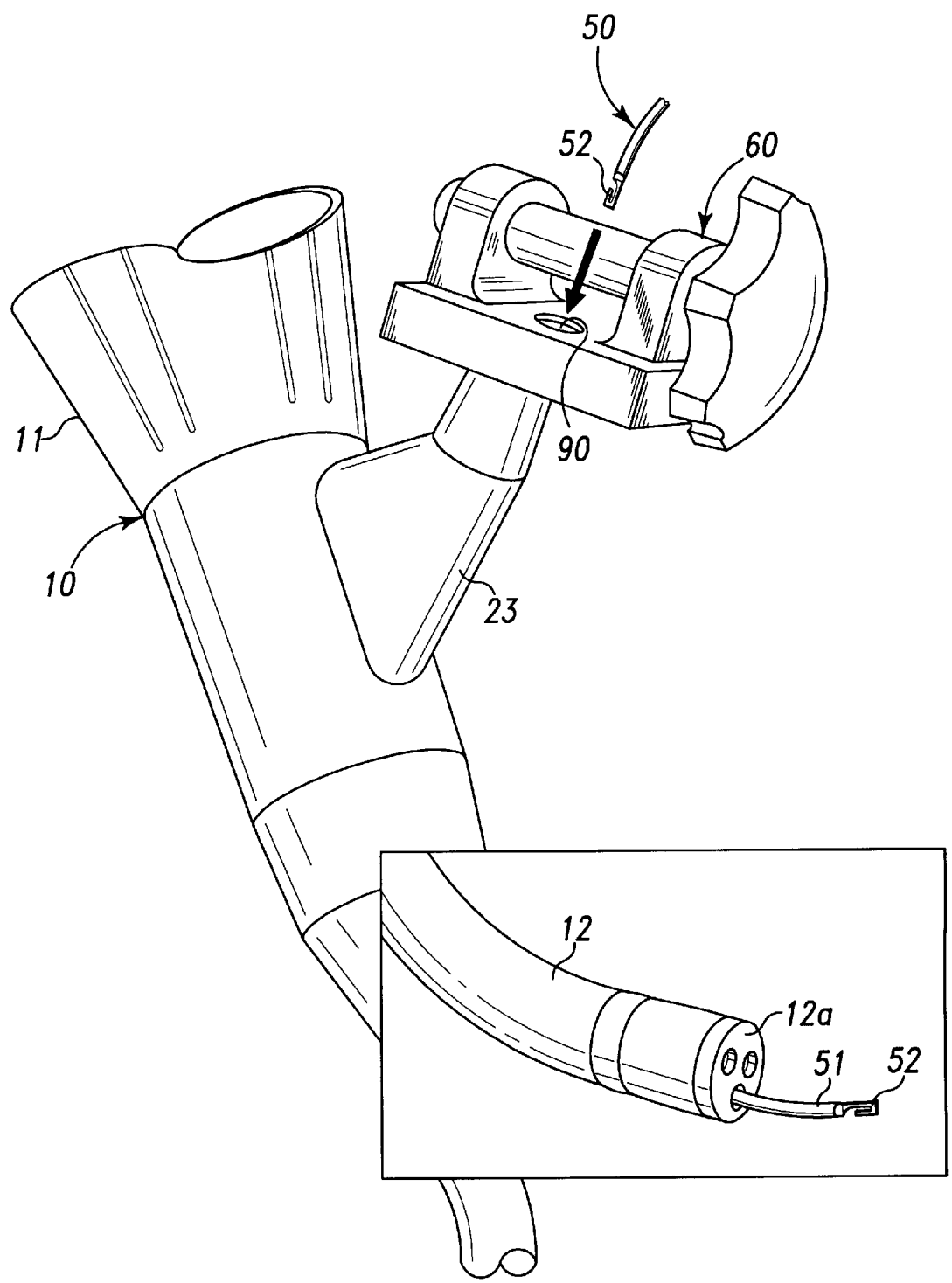
FIG. 14 is an enlarged perspective view of activating mechanism 60 in use with an endoscopic ligating apparatus 10 and showing the use of the loading catheter 50 of FIG. 5, with an inset view showing a loading hook 52 extending from the insertion end of the endoscopic ligating apparatus.
Figure 15:
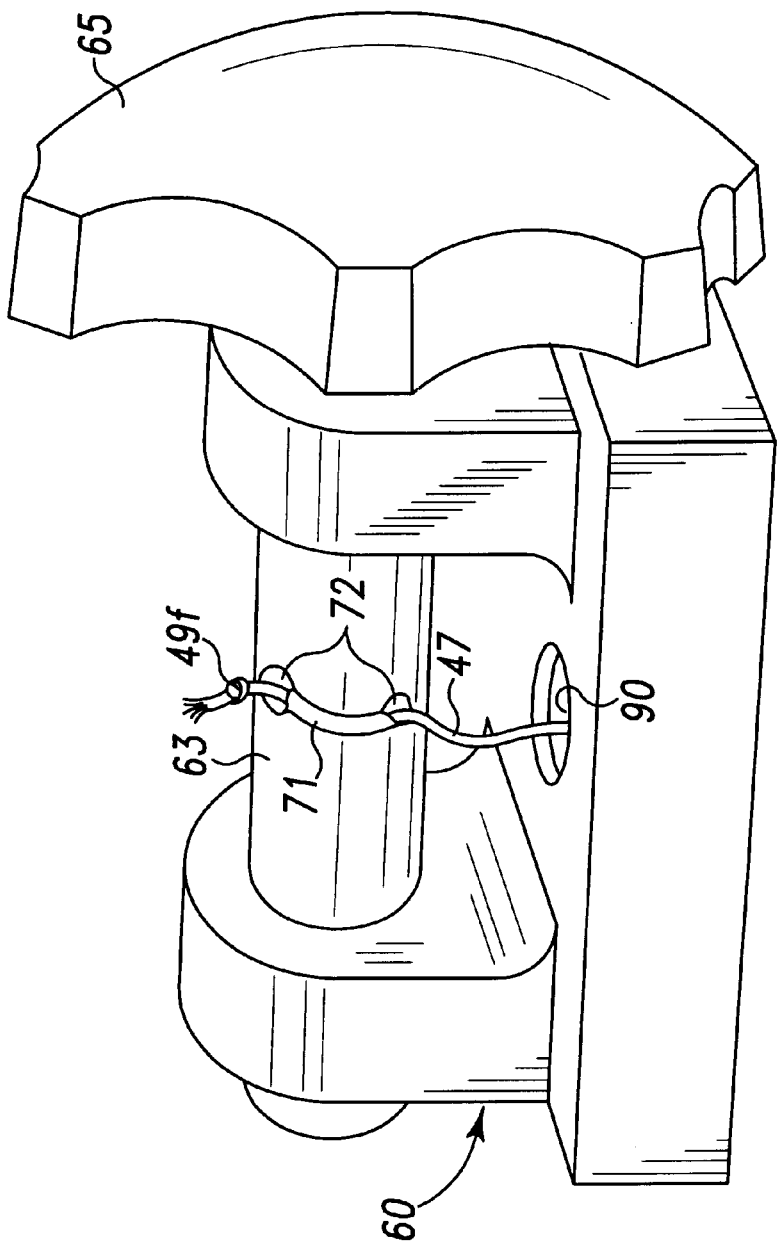
FIG. 15 is a perspective view of the activating mechanism 60 of FIG. 14 shown with the trip wire engaged to the drive spool.

In using the endoscopic ligation apparatus of the present invention, the loading catheter 50 can be projected with a loading hook 52 extending through the stem bore 90 of the activating mechanism 60. Preferably, the loading hook 52 resiliently deforms the slit 101 in the seal 68 as the tubular body 51 of the loading catheter 50 is threaded through the mounting component 61 and into the working channel 19. The loading catheter 50 is continuously pushed through the working channel until it projects out the proximal end 12a of the flexible endoscope section 12, as shown in the inset in FIG. 14. At that point, the locking knot 49f of the trip wire 45 can be arranged within the slot 56 in the loading hook 52 so that the hook engages the trip wire. The loading catheter 50 can then be manually retracted through the working channel 18 until the proximal end of the trip wire 45 and the locking knot 49f exits the stem bore 90 of the base portion 62. This free end of the trip wire 45 can then be oriented within the slot 71 in the spool 63, as shown in FIG. 15. Preferably, the locking knot 49f is pressed into one of the enlarged recesses 72 with the braided strand 47 of the trip wire extending through the slot 71 and exiting the opposite enlarged recess 72 of the spool 63.

In accordance with one specific embodiment, any slack in the trip wire 45 can be taken up by rotating the knob 65 of the activating mechanism 60. At this point, the drive pin 64 is pulled outward away from the clutch 67 so that the free wheel portion 79 is disposed within the clutch 67. The knob 65 can then be freely rotated in any direction as may be required to properly seat the locking knot 49f and trip wire 45 on the spool 63. As the spool 63 is rotated, the trip wire 45 is wound onto the spool and the endoscopic ligator 30 drawn closer to the insertion end 12a of the flexible endoscope section 12. Once the ligator 30 is sufficiently close, the friction adapter 35 can be manually engaged about the cylindrical surface 12b of the flexible endoscope section 12 to firmly secure the ligator thereon. Any slack in the trip wire 45 can then be taken up by rotating the knob 65 and spool 63.

With the flexible endoscopic ligation assembly 10 complete, the insertion end 12a and ligator 30 can be directed to a subject tissue to be ligated. This activity can occur under direct vision through the viewing channel 17 and viewing end 14 of the endoscopic instrument. Once the tissue to be ligated has been located, suction can be applied to draw the tissue toward the insertion end 12a of the flexible endoscope section 12. At this point, the knob 65 of the activating mechanism 60 can be pushed in so that the one-way drive portion 80 of the drive pin 64 is within the clutch 67. In this orientation, the knob 65, and therefore the spool 63, can be rotated in only one direction. With the target tissue directly adjacent the proximal end 12*a*, the knob 65 and spool 63 can be rotated to draw the trip wire 45. As the trip wire 45 is pulled, the first locking beads 49*a* of each of the trip strands 46 pull a first ligating band 40 off of the barrel 31. Once the ligating band 40 is pulled off of the barrel, it resiliently snaps back to its constricted diameter about the target tissue. The loops 46*a* of the separate trip strands 46 are then taken up by further rotation of the spool 63 until the trip wire 45 is slightly taut. At this point, then, the insertion end 12*a* of the flexible endoscope section 12 can be manipulated to another ligation site at which time the process is repeated to dispense a second ligating band 40.

The specification of PCT application Serial No. PCT/US96/14,374 filed Sep. 6, 1996 entitled Channel Mounted Activating Mechanism for an Endoscopic Ligator, Peifer et al. inventors, is hereby incorporated by reference.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:

1. An endoscopic ligation apparatus for use with a flexible endoscope having a plurality of channels therethrough including a working channel opening at an auxiliary port, said apparatus comprising:
   a hollow barrel defining an outer surface and a hollow interior therethrough, and including a distal end and a proximal end;
   means for mounting said proximal end of said barrel to the insertion end of the flexible endoscope;
   at least one elastic ligating band removably mounted on said outer surface of said barrel; and
   a trip wire configured to extend through the working channel of the endoscope and including;
      a proximal end and a distal end, and a length between said ends sufficient for said distal end to extend beyond the insertion end of the endoscope while the proximal end extends from the auxiliary port;
      a plurality of strands at said distal end, each of said strands extending through said hollow interior of said barrel beyond said distal end of said barrel and overlaying said outer surface of said barrel underneath said at least one ligating band; and
      each of said plurality of strands including a least one bead attached thereto and situated adjacent said at least one ligating band between said band and said proximal end of said barrel, whereby tension applied to said proximal end of said trip wire pulls each of said plurality of strands toward said distal end of said barrel such that said bead on each of said strands engage said at least one ligating band to dislodge said band from said barrel,
   wherein said trip wire includes a bead attached thereto adjacent said proximal end.

2. An endoscopic ligation apparatus for use with a flexible endoscope having a plurality of channels therethrough including a working channel opening at an auxiliary port, said apparatus comprising:
   a hollow barrel defining an outer surface and a hollow interior therethrough, and including a distal end and a proximal end;
   means for mounting said proximal end of said barrel to the insertion end of the flexible endoscope;
   at least one elastic ligating band removably mounted on said outer surface of said barrel; and
   a trip wire configured to extend through the working channel of the endoscope and including;
      a proximal end and a distal end, and a length between said ends sufficient for said distal end to extend beyond the insertion end of the endoscope while the proximal end extends from the auxiliary port;
      a plurality of strands at said distal end, each of said strands extending through said hollow interior of said barrel beyond said distal end of said barrel and overlaying said outer surface of said barrel underneath said at least one ligating band; and
      each of said plurality of strands including a least one bead attached thereto and situated adjacent said at least one ligating band between said band and said proximal end of said barrel, whereby tension applied to said proximal end of said trip wire pulls each of said plurality of strands toward said distal end of said barrel such that said bead on each of said strands engage said at least one ligating band to dislodge said band from said barrel,
   wherein said trip wire includes a braided portion between said proximal end and said plurality of strands, said braided section being formed by braiding said plurality of strands together.

3. The endoscopic ligation apparatus according to claim 2, wherein said trip wire includes an additional strand having a first portion braided together with said plurality of strands in said braided portion, and a second portion wrapped around said plurality of strands between said braided portion and said distal end of said trip wire.

4. An endoscopic ligation kit for use with a flexible endoscope having a working channel extending between an insertion end and an auxiliary port, said kit comprising:
   a hollow barrel defining a hollow interior and an outer surface;
   means for engaging said barrel to the insertion end of an endoscope;
   at least one elastic ligating band stretched around said barrel on said outer surface;
   a trip wire extending through said hollow interior of said barrel and configured to extend through the working channel of the endoscope with a distal end projecting beyond the insertion end of the endoscope and a proximal end projecting beyond the auxiliary port, said trip wire including a plurality of strands overlying said outer surface of said barrel underneath said at least one ligating band;
   a loading catheter sized to be slidably extended through the working channel of the endoscope, said loading catheter including a tubular body and a loading hook connected at one end of said tubular body, said loading hook configured to engage the proximal end of said trip wire to draw said trip wire through the working channel of the endoscope;
   wherein said trip wire includes a bead attached thereto adjacent said proximal end of said trip wire, said bead having an outside dimension; and
   said loading hook of said loading catheter defines a slot, said slot having a width less than the outside dimension of said bead.

5. An endoscopic ligation kit for use with a flexible endoscope having a working channel extending between an insertion end and an auxiliary port, said kit comprising:

a hollow barrel defining a hollow interior and an outer surface;

means for engaging said barrel to the insertion end of an endoscope;

at least one elastic ligating band stretched around said barrel on said outer surface;

a trip wire extending through said hollow interior of said barrel and configured to extend through the working channel of the endoscope with a distal end projecting beyond the insertion end of the endoscope and a proximal end projecting beyond the auxiliary port, said trip wire including a plurality of strands overlying said outer surface of said barrel underneath said at least one ligating band;

a loading catheter sized to be slidably extended through the working channel of the endoscope, said loading catheter including a tubular body and a loading hook connected at one end of said tubular body, said loading hook configured to engage the proximal end of said trip wire to draw said trip wire through the working channel of the endoscope;

wherein said tubular body is hollow; and said loading hook includes a mounting shank configured to fit snugly within said hollow tubular body.

6. The endoscopic ligation kit according to claim 5, wherein said mounting shank of said loading hook includes a number of annular barbs defined thereon configured to resist dislodgement of said mounting shank from within said hollow tubular body.

7. An endoscopic ligation kit for use with a flexible endoscope having a working channel extending between an insertion end and an auxiliary port, said kit comprising:

a hollow barrel defining a hollow interior and an outer surface;

means for engaging said barrel to the insertion end of an endoscope;

at least one elastic ligating band stretched around said barrel on said outer surface;

a trip wire extending through said hollow interior of said barrel and configured to extend through the working channel of the endoscope with a distal end projecting beyond the insertion end of the endoscope and a proximal end projecting beyond the auxiliary port, said trip wire including a plurality of strands overlying said outer surface of said barrel underneath said at least one ligating band;

a loading catheter sized to be slidably extended through the working channel of the endoscope, said loading catheter including a tubular body and a loading hook connected at one end of said tubular body, said loading hook configured to engage the proximal end of said trip wire to draw said trip wire through the working channel of the endoscope;

further comprising an activation mechanism including:
a spool for winding said trip wire thereon;
means for rotating said spool; and
means for stably mounting said mechanism to the auxiliary port of the endoscope.

8. The endoscopic ligation kit according to claim 7 wherein said activation mechanism includes:

a drive pin supporting said spool;
a one-way roller clutch rotatably supporting said drive pin; and
a base portion supporting said drive pin and said clutch.

9. The endoscopic ligation kit according to claim 8, wherein said drive pin includes a first portion having a diameter sized to engage said clutch and an adjacent second portion having a diameter sized to freely rotate within said clutch.

10. An endoscopic ligation kit for use with a flexible endoscope having a working channel extending between an insertion end and an auxiliary port, said kit comprising:

a hollow barrel defining a hollow interior and an outer surface;

means for engaging said barrel to the insertion end of an endoscope;

at least one elastic ligating band stretched around said barrel on said outer surface;

a trip wire extending through said hollow interior of said barrel and configured to extend through the working channel of the endoscope with a distal end projecting beyond the insertion end of the endoscope and a proximal end projecting beyond the auxiliary port, said trip wire including a plurality of strands overlying said outer surface of said barrel underneath said at least one ligating band;

a loading catheter sized to be slidably extended through the working channel of the endoscope, said loading catheter including a tubular body and a loading hook connected at one end of said tubular body, said loading hook configured to engage the proximal end of said trip wire to draw said trip wire through the working channel of the endoscope;

further comprising an activation mechanism including:
a spool for winding said trip wire thereon;
means for rotating said spool; and
mounting means for stably mounting said mechanism to the auxiliary port of the endoscope.

11. The endoscopic ligation kit according to claim 10, wherein:

said activation mechanism includes a base portion carrying said means for rotating said spool; and said mounting means includes;
a bore defined in said base portion; and
a mounting component having a first portion configured to engage said base at said bore, said mounting component defining a threading bore therethrough sized to slidably receive said trip wire, said mounting component including a second portion configured to extend into the working channel of the auxiliary port of the endoscope.

12. The endoscopic ligation kit according to claim 11 further comprising an irrigation adaptor including:

a hollow tip sized to extend through said bore in said base portion and into said threading bore of said mounting component; and a hub configured to engage a source of irrigation fluid.

* * * * *

UNITED STATES PATENT AND TRADEMARK OFFICE
CERTIFICATE OF CORRECTION

PATENT NO : 6,007,551

DATED : December 28, 1999

INVENTOR(S) : Peifer et al.

It is certified that error appears in the above-identified patent and that said Letters Patent are hereby corrected as shown below:

On the front page, right column, In the ABSTRACT, line 2, delete the word "percutaneuously".

Signed and Sealed this

Seventeenth Day of April, 2001

*Attest:*

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO.      : 6,007,551
DATED           : December 28, 1999
INVENTOR(S)     : Peifer et al.

It is certified that error appears in the above-identified patent and that said Letters Patent is hereby corrected as shown below:

<u>Title page, Item [73],</u>
In the assignee, add -- DabeGran Technologies, Inc., St. Louis, Missouri --.

Signed and Sealed this

Fourth Day of September, 2001

Attest:

Attesting Officer

NICHOLAS P. GODICI
*Acting Director of the United States Patent and Trademark Office*

UNITED STATES PATENT AND TRADEMARK OFFICE
CERTIFICATE OF CORRECTION

PATENT NO. : 6,007,551
DATED : December 28, 1999
INVENTOR(S) : Peifer et al.

It is certified that error appears in the above-identified patent and that said Letters Patent is hereby corrected as shown below:

Title page, RELATED U.S. APPLICATION DATA,
Line 2, remove the word "abandoned" and replace it with -- Pat. No. 5,735,861 --.

Column 1,
Line 6, remove the word "abandoned" and replace it with -- U.S. Pat. No. 5,735,861 --.

Signed and Sealed this

Sixth Day of November, 2001

*Attest:*

NICHOLAS P. GODICI
*Attesting Officer*    Acting Director of the United States Patent and Trademark Office